United States Patent
Deborski et al.

(10) Patent No.: US 9,597,099 B2
(45) Date of Patent: Mar. 21, 2017

(54) ENERGY-BASED TREATMENT METHODS FOR REFRACTORY GOUT

(71) Applicant: COVIDIEN LP, Mansfield, MA (US)

(72) Inventors: Christopher A. Deborski, Denver, CO (US); Anthony B. Ross, Boulder, CO (US); William H. Nau, Jr., Longmont, CO (US); David J. Van Tol, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 136 days.

(21) Appl. No.: 14/252,856

(22) Filed: Apr. 15, 2014

(65) Prior Publication Data

US 2015/0032046 A1 Jan. 29, 2015

Related U.S. Application Data (60) Provisional application No. 61/859,616, filed on Jul. 29, 2013.

(51) Int. Cl.
| | |
|---|---|
| A61B 17/22 | (2006.01) |
| A61M 1/00 | (2006.01) |
| A61N 5/00 | (2006.01) |
| A61N 5/02 | (2006.01) |
| A61N 7/00 | (2006.01) |
| A61B 18/14 | (2006.01) |
| A61B 18/18 | (2006.01) |

(Continued)

(52) U.S. Cl.
CPC ...... *A61B 17/22004* (2013.01); *A61B 18/148* (2013.01); *A61B 18/1815* (2013.01); *A61M 1/0084* (2013.01); *A61N 5/00* (2013.01); *A61N 5/022* (2013.01); *A61N 7/00* (2013.01); *A61B 2018/00642* (2013.01); *A61N 5/045* (2013.01); *A61N 5/062* (2013.01)

(58) Field of Classification Search
CPC ........ A61B 18/148; A61B 2018/00642; A61B 18/1815; A61N 7/00; A61N 5/045; A61N 1/40; A61N 5/062
See application file for complete search history.

(56) References Cited

U.S. PATENT DOCUMENTS 5,658,322 A * 8/1997 Fleming ................... A61N 1/40
607/50
5,690,109 A * 11/1997 Govind .................. A61N 2/002
324/315

(Continued)

OTHER PUBLICATIONS

Centers for Disease Control and Prevention: CDC 24/7: Saving Lives. Protecting People. "Gout", pp. 1-4, http://www.cdc.gov/arthritis/basics/gout.htm last visited Jun. 16, 2014.

(Continued)

*Primary Examiner* — Imani Hayman
*Assistant Examiner* — Hamza Darb (57) ABSTRACT

A method of performing a medical procedure is disclosed. The method includes: positioning an energy delivery device configured to deliver energy adjacent uric acid (UA) crystals having a resonance frequency; applying energy to tissue through the energy delivery device at a predetermined frequency thereby resonating the UA crystals; debulking at least a portion of the UA crystals; and removing at least a portion of the debulked UA crystals.

18 Claims, 5 Drawing Sheets

(51) Int. Cl.
*A61N 5/04* (2006.01)
*A61N 5/06* (2006.01)
*A61B 18/00* (2006.01)

(56) References Cited

U.S. PATENT DOCUMENTS

| | | |
|---|---|---|
| 6,638,981 B2 | 10/2003 | Williams et al. |
| 7,105,011 B2 | 9/2006 | Auge, II |
| 7,229,455 B2 | 6/2007 | Sakurai et al. |
| 2003/0178030 A1* | 9/2003 | Constantz ............. A61B 17/22 128/898 |
| 2004/0015105 A1 | 1/2004 | Ito et al. |
| 2006/0020260 A1* | 1/2006 | Dover ................. A61B 18/203 606/9 |
| 2006/0116693 A1* | 6/2006 | Weisenburgh, II .................... A61B 17/12099 606/128 |
| 2008/0046053 A1 | 2/2008 | Wagner et al. |
| 2009/0105142 A1* | 4/2009 | Moscicki ........... C07K 14/8114 514/1.1 |
| 2009/0177123 A1 | 7/2009 | Peterson |
| 2011/0238083 A1* | 9/2011 | Moll .................... A61B 17/062 606/130 |
| 2011/0245734 A1 | 10/2011 | Wagner et al. |
| 2013/0131804 A1* | 5/2013 | Barry ................... C12N 5/0663 623/14.12 |

OTHER PUBLICATIONS

Medline Plus Trusted Health Information for You: "Gout", pp. 1-4, http://www.nlm.nih.gov/medlineplus/ency/article/000422.htm , last visited Jun. 16, 2014.

Wikipedia: "Gout overview", pp. 1-2 http://www.wikidoc.org/index.php?title=Gout_overview&printable=yes, last visited Jun. 16, 2014.

Science Daily "Gout prevalence swells in U.S. over last two decades; Increase in obesity and hypertension are likely contributors", pp. 1-2, http://www.sciencedaily.com/releases/2011/07/110728082551.htm , last visited Jun. 15, 2014.

Arromdee et al., The Journal of Rheumatology: "Epidemiology of gout: is the incidence rising?", pp. 1-4, http://jrheum.org/content/29/11/2403.abstract, last visited, Jun. 16, 2014.

* cited by examiner

ENERGY-BASED TREATMENT METHODS FOR REFRACTORY GOUT

CROSS REFERENCE TO RELATED APPLICATION

The present application claims the benefit of and priority to U.S. Provisional Application Ser. No. 61/859,616, filed on Jul. 29, 2013, the entire contents of which are incorporated herein by reference.

BACKGROUND

1. Technical Field

The present disclosure generally relates to apparatus, systems and methods for interventional and non-interventional treatment of refractory gout.

2. Description of Related Art

Gout is a complex form of arthritis characterized by sudden, severe attacks of pain, redness and tenderness in joints, often the joint at the base of the big toe. Symptoms of gout include sudden occurrence of pain in the large joint of the big toe, although gout can occur in feet, ankles, knees, hands and wrists. The pain is likely to be most severe within the first 12 to 24 hours after it begins with lingering joint discomfort that may last from a few days to a few weeks after the most severe pain subsides.

Gout occurs when urate crystals (hereinafter "UA crystals") are deposited and accumulate in joints, causing the inflammation and intense pain of a gout attack. UA crystals are formed when excessive amount of uric acid accumulate in the circulatory system. UA crystals are characterized by sharp, needle-like crystalline structures that, when deposited in tendons, joints, kidneys, and other organs, results in the joint or surrounding tissue to become inflamed, swollen, tender and red.

The body produces uric acid when the digestive system breaks down purines. Purines are natural substances found in all of the body's cells, as well as in virtually all foods. A relatively high small number of foods, mostly high protein foods, contain concentrated amounts of purines such as, but not limited to, organ meats, fish, certain vegetables, game, poultry and yeast. The breakdown of the genetic material (e.g., cells) also results in the breakdown of purines contained therein, thereby forming uric acid. Normally uric acid remains dissolved in the blood circulating through the body and naturally passing through the kidneys and into urine. At normal levels, the uric acid serves as an antioxidant that helps prevent damage to blood vessel linings. As such, a healthy supply of uric acid is important for protecting blood vessels and the circulatory system.

Occasionally, the body produces too much uric acid and/or the kidneys fail to extract and/or regulate the amount of uric acid in the blood. The build-up of uric acid may be due to excessive breakdown of cells thereby exceeding the kidney's ability to extract uric acid or the build-up may be due to poor kidney function.

Gout may develop into more severe conditions such as recurrent gout, advanced gout and kidney stones. Recurrent gout results in experiencing gout symptoms several times a year. Medications may help prevent recurrent gout attacks. Advanced gout results in deposits of UA crystals under the skin in nodules called tophi. Tophi can develop in several areas such as, but not limited to, fingers, hands, feet, elbows, Achilles tendons along the back of the ankles and combinations thereof. Tophi can become swollen, tender and under extreme conditions, the tophi can rupture. UA crystals may also collect in the urinary tract resulting in the formation of kidney stones.

UA crystals may be present in the joint for a long time without causing symptoms. Infection, injury to the joint, surgery, drinking too much alcohol, or eating the wrong kinds of foods may suddenly bring on the symptoms, which include pain, tenderness, redness, warmth, and swelling of the joint. Gout attacks typically begin at night when the body temperature of the extremities lowers resulting in the crystallization of the uric acid from liquid to crystal.

During bouts of gout, the inflamed skin over the affected joint may be red, shiny, and dry, and the inflammation may be accompanied by a mild fever. The symptoms may continue for weeks, months or years. Over the course of time, attacks of gout may recur more frequently, last longer, and affect more joints. Eventually, the tophi form stone-like deposits that build up in the joints, ligaments, and tendons, which can lead to permanent joint deformity and decreased motion.

When gout remains untreated or undertreated, the intercritical periods typically become shortened, and the attacks, although sometimes less intense, can last longer. Over the long term, from about 10 to about 20 years, or less, gout can become a chronic disorder characterized by constant low-grade pain and mild or acute inflammation. Gout may eventually affect several joints, including those that may have been free of symptoms at the first appearance of the disorder.

Gout, while not curable, may be managed by medications that lower the level of uric acid in the body and/or addressing lifestyle factors that increase the risk of developing gout. The longer treatment for the underlying causes of gout is delayed, the more UA crystals are deposited in joints. Unfortunately, each episode of gout leaves deposits of UA crystals in the joints, and, in particular, in the joint of the great toe.

The present disclosure describes minimally invasive and non-invasive methods, system and apparatuses to breakdown UA crystals and/or remove from joints in the body.

SUMMARY

According to an embodiment of the present disclosure, a method of performing a medical procedure is disclosed. The method includes: positioning an energy delivery device configured to deliver energy adjacent uric acid (UA) crystals having a resonance frequency; applying energy to tissue through the energy delivery device at a predetermined frequency thereby resonating the UA crystals; debulking at least a portion of the UA crystals; and removing at least a portion of the debulked UA crystals.

According to one aspect of the above embodiment, the energy is selected from the group consisting of mechanical energy, electrical energy, and combinations thereof.

According to one aspect of the above embodiment, the energy delivery device is a mechanical energy delivery device configured to resonate at least a portion of the UA crystals with ultrasonic energy.

According to one aspect of the above embodiment, the energy delivery device is a radiofrequency (RF) energy delivery device configured to resonate at least a portion of the UA crystals with RF energy.

According to one aspect of the above embodiment, the energy delivery device is a microwave energy delivery device configured to resonate at least a portion of the UA crystals with microwave energy.

According to one aspect of the above embodiment, the method further includes: providing a fluid to the joint of the patient; suspending at least a portion of the debulked UA crystals in the fluid; and removing the fluid and the suspended debulked UA crystals from the joint of the patient.

According to one aspect of the above embodiment, debulking of at least a portion of the UA crystals further comprises separating the portion of the UA crystals from a UA crystal mass attached to surrounding tissue.

According to one aspect of the above embodiment, debulking of at least a portion of the UA crystals further comprises separating the portion of the UA crystal mass into two or more constituent portions.

According to another embodiment of the present disclosure, a method of performing a medical procedure is disclosed. A method of performing a medical procedure includes: adjusting pH of a circulatory system fluid; positioning an energy delivery device configured to deliver energy adjacent uric acid (UA) crystals having a resonance frequency; applying energy to tissue through the energy delivery device at a predetermined frequency thereby resonating the UA crystals; debulking at least a portion of the UA crystals; and removing at least a portion of the debulked UA crystals.

According to one aspect of the above embodiment, the pH is adjusted to from about 6.0 to about 7.2.

According to one aspect of the above embodiment, pH is adjusted via dialysis.

According to one aspect of the above embodiment, the energy delivery device is a mechanical energy delivery device configured to resonate at least a portion of the deposit of UA crystals with ultrasonic energy.

According to one aspect of the above embodiment, the energy delivery device is a radio frequency (RF) energy delivery device configured to resonate at least a portion of the deposit of UA crystals with RF energy.

According to one aspect of the above embodiment, the RF energy delivery device is driven at a harmonic of the resonant frequency.

According to one aspect of the above embodiment, the energy delivery device is a light-based energy delivery device configured to resonate at least a portion of the UA crystals with light energy.

According to one aspect of the above embodiment, the energy delivery device is a microwave energy delivery device configured to resonate at least a portion of the UA crystals with microwave energy.

According to one aspect of the above embodiment, the microwave energy delivery device is driven at a harmonic of the resonant frequency.

According to one aspect of the above embodiment, the method further includes injecting an injection fluid into the tissue to adjust the pH of the circulatory system fluid, wherein the injection fluid has a pH different from the pH of the circulatory system fluid.

According to another embodiment of the present disclosure, an apparatus for performing a medical procedure is disclosed. The apparatus includes an energy delivery device including a distal energy delivery portion configured to resonate a deposit of UA crystals formed in tissue at a resonant frequency or a harmonic thereof, the distal energy delivery portion configured to convert at least a portion of the deposit of UA crystals to uric acid.

According to one aspect of the above embodiment, the apparatus further includes: a supply lumen to supply a fluid to dissolve the uric acid; and a return lumen to withdraw the fluid including the uric acid.

BRIEF DESCRIPTION OF THE DRAWINGS

Various embodiments of the present disclosure are described herein below with reference to the figures wherein.

DETAILED DESCRIPTION

Particular embodiments of the present disclosure are described below with reference to the accompanying drawings; however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In this description, as well as in the drawings, like-referenced numbers represent elements, which may perform the same, similar or equivalent functions.

As gout progresses from an acute condition to a chronic condition, uric acid crystals (hereinafter "UA crystals") are deposited in joints. These crystals can persist for long periods of time and depending on the success of treatment for the primary cause of gout, can accumulate over time. These remnant crystal accumulations will cause or exacerbate acute gout inflammation and produce joint erosion. In only extreme cases of chronic refractory gout is treatment for accumulation UA crystal masses considered. The common treatment is invasive surgical extraction.

Since surgical extraction and/or reduction of UA crystal masses is only considered in extreme cases, a vast majority of individuals with UA crystal masses who are not candidates for surgical extraction have little recourse but to live with the pain, tenderness, redness and swelling of the joint associated with the UA crystal masses. The minimally invasive and non-invasive systems, methods and devices described herein provide medical alternatives to individuals who are not candidates for invasive surgical treatments.

Figure 1:
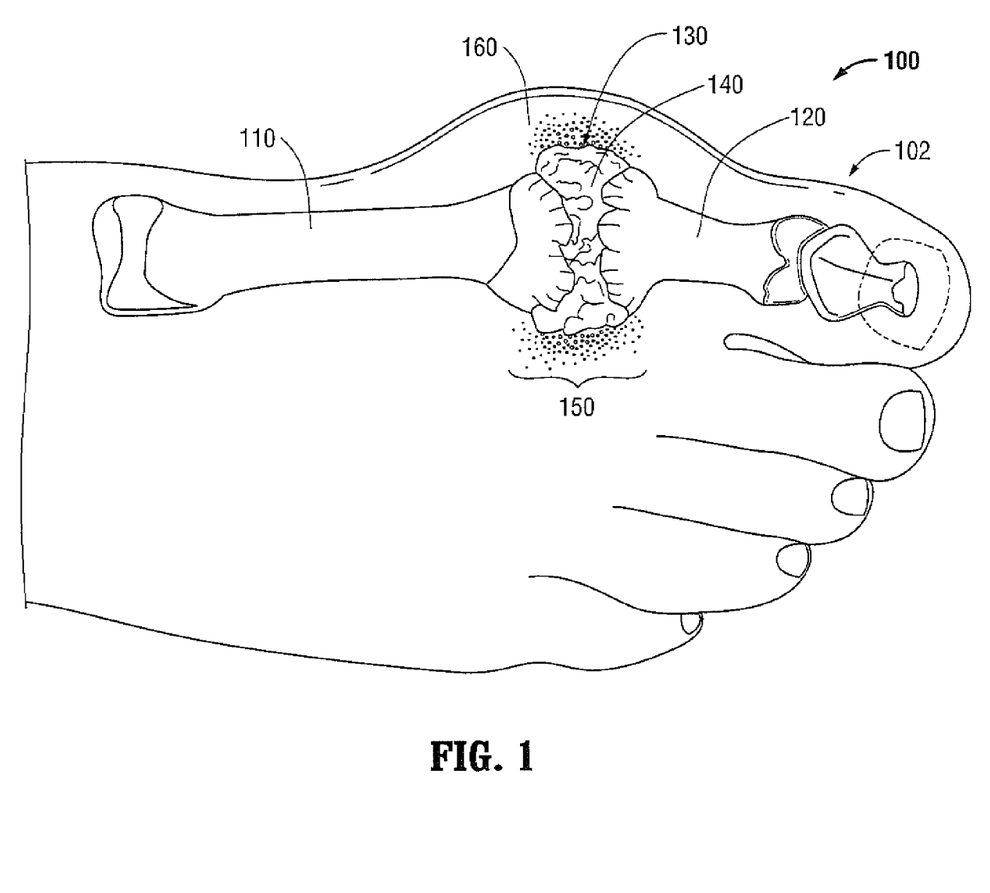
FIG. 1 illustrates a foot with a great toe joint affected by acute gout.

Referring to FIG. 1, the distal portion of a human foot 100 illustrates the effect of gout on the metatarsal-phalangeal joint 130 (hereinafter "MP joint 130"). The MP joint 130 connects a first bone (e.g., metatarsus) 110 to a second bone (e.g., proximal phalange 120) of a great toe 102. The foot 100 also includes deposits of free-floating UA crystals 150 in the tissue surrounding the MP joint 130 and massed UA crystals 140 attached to the MP joint 130. UA crystals 140, 150 contribute to swelling 160 of the surrounding tissue. While the systems, methods and devices illustrated and described herein treat UA crystals 140, 150 in the MP joint 130, any joint or tissue within the body may be similarly treated.

Figure 2:
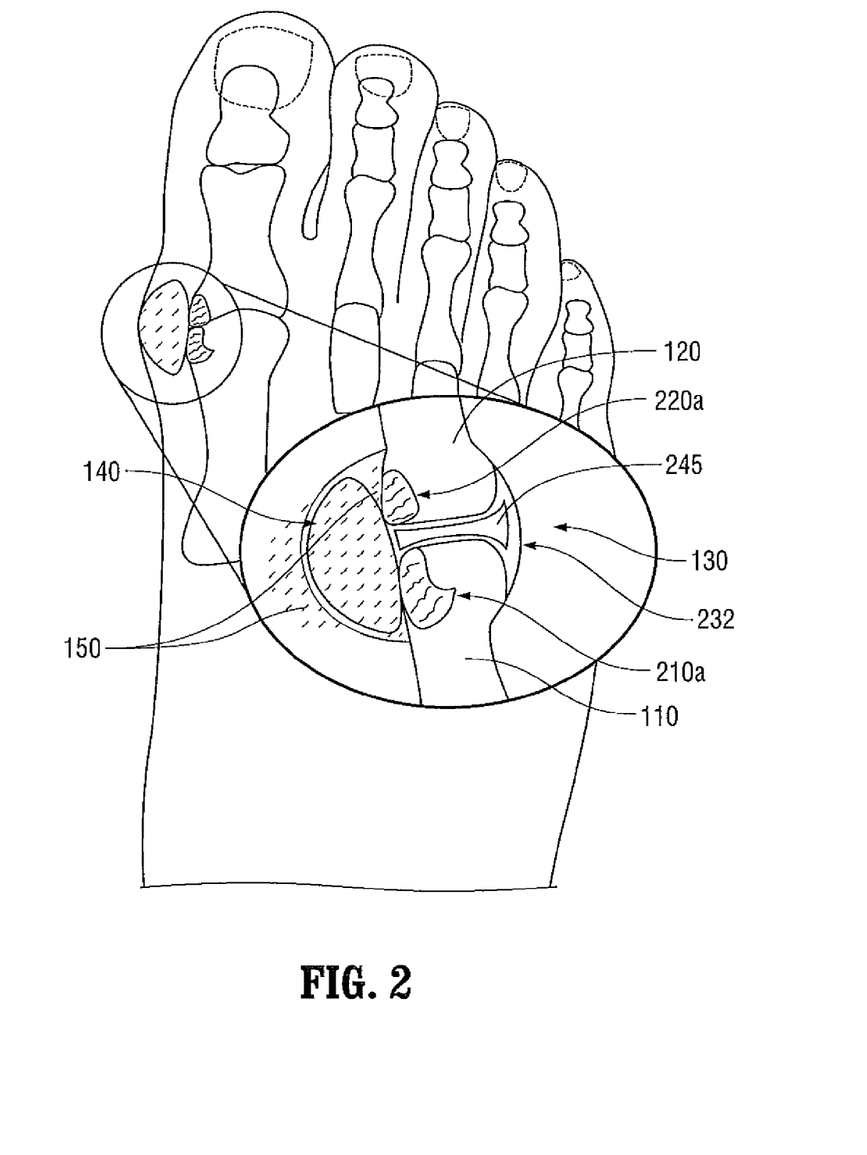
FIG. 2 is an enlarged illustration of a synovium of the great toe joint of FIG. 1 affected by acute gout.

FIG. 2 illustrates a synovium 232 of an MP joint 130, affected by gout. The synovium 232 includes free-floating UA crystals 150 in a synovial fluid 332a (FIG. 3) and the massed UA crystals 140 attached to various areas of the MP joint 130, which results in bone erosion 220a of the bone 120 and bone erosion 220b of the metatarsal of the bone 110.

The UA crystals 140, 150 may also cause damage to the articulating surfaces of the bones 110, 120 and/or connective tissue 245 that form the MC joint 130. Connective tissue 245 may include bone-to-bone connective tissue, including, but not limited to, ligaments (e.g., planar ligaments, collateral ligaments, dorsal ligaments, interosseous ligaments), cartilage, and combinations thereof. Connective tissue 245 may also include muscle-to-bone connective tissue (e.g., tendons).

Figure 3:
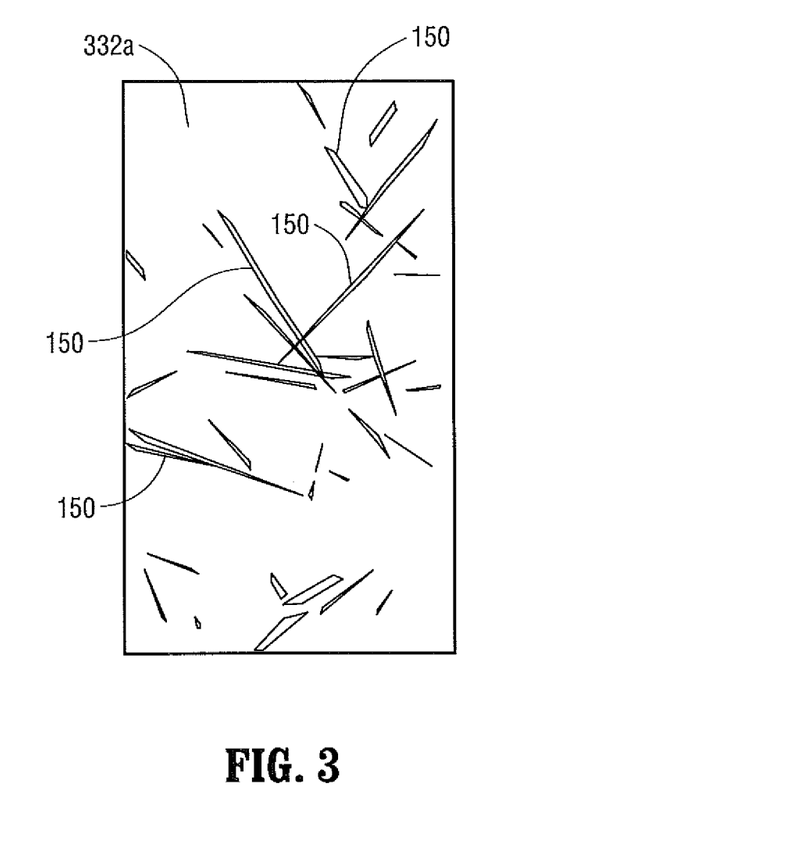
FIG. 3 is a magnified image of synovial fluid, extracted from the synovium and containing UA crystals.

FIG. 3 is a magnification of UA crystals 150 floating in synovial fluid 332a. UA crystals 150 form elongate needle-like structures. As the synovial fluid 332a is saturated with uric acid, UA crystals 140, 150 are formed and attach to the various structures in the MP joint 130 (FIGS. 1 and 2) and or remain suspended in the synovial fluid 332a (FIGS. 1-3). As can be appreciated, surgical removal of the free-floating UA crystals 140, 150 present significant, and different, surgical challenges.

A minimally invasive medical procedure according to the present disclosure to remove the UA crystals 140, 150 includes accessing the UA crystals 140, 150 in the synovium 232, applying energy to the UA crystals 140, 150, debulking the UA crystals 140, 150 and removing UA crystals 140, 150 and/or uric acid (formed from a portion of the debulked UA crystals 140, 150) from the synovium 232. As used herein, minimally invasive medical procedures refer to endoscopic procedures where the energy delivery device is passed through an introducer to reach the surgical site.

Figure 4:
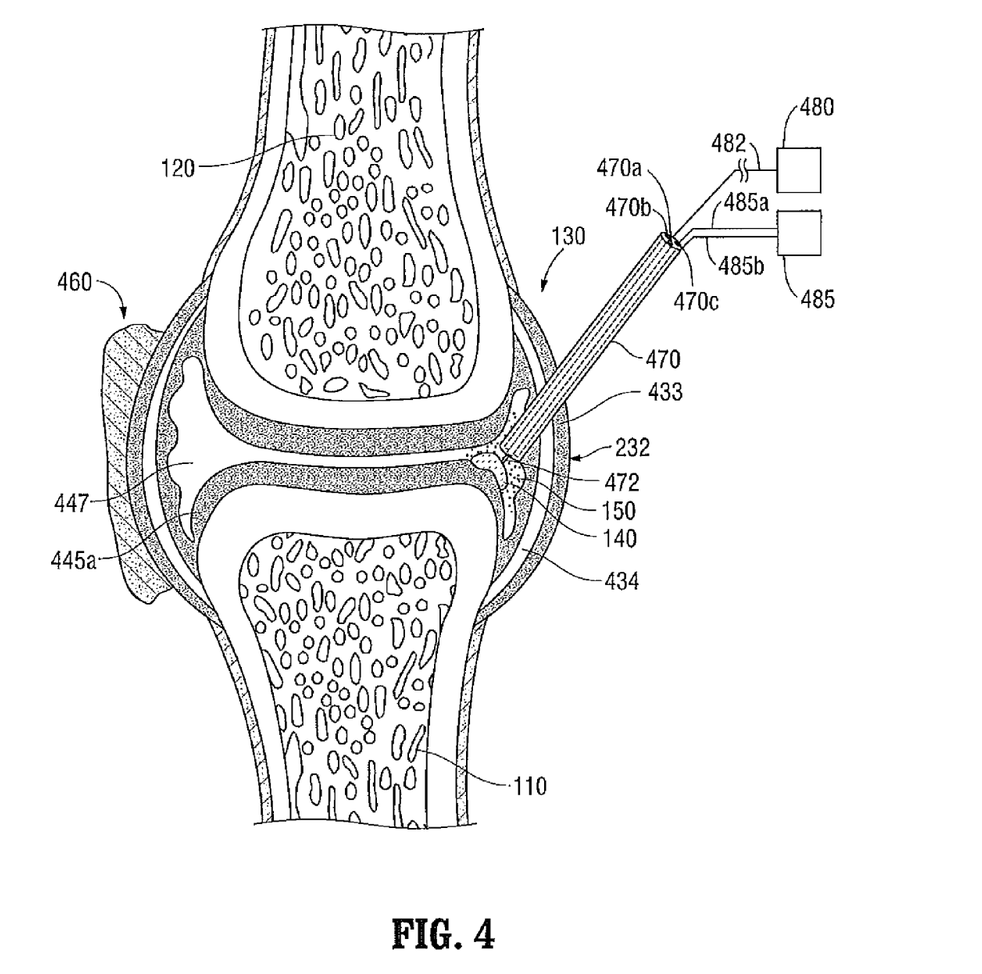
FIG. 4 illustrates a system and apparatus for internally debulking UA crystals from the synovium of FIG. 2 according to embodiments of the present disclosure.

As illustrated in FIG. 4, an introducer lumen 470 penetrates an outer fibrous layer 433 and loose soft tissue 434 of the synovium 232. The distal tip of the introducer lumen 470 is positioned to provide access to articular space 447 of the MP joint 130. During initial penetration, introducer lumen 470 may include an interchangeable element (not explicitly shown) that prevents material from penetrating the interior lumen of the introducer 470. The interchangeable element may be removed from the introducer lumen 470 after the distal tip is properly positioned.

Introducer lumen 470 may include a plurality of channels 470a-470c for accessing the articular space 447 of the MP joint 130. In embodiments, a device channel 470a may accommodate the insertion of an energy delivery device 472, a supply channel 470b may supply aspiration fluid to the articular space 447 and a return channel 470c may provide negative pressure to the articular space 447 for removing aspiration fluid, free-floating UA crystals 150 and/or uric acid suspended in fluid.

Energy delivery device 472 is introduced into the articular space 447 of the MP joint 130 through the device channel 470a of the introducer lumen 470. Energy delivery device 472 is coupled to an energy supply 480 via an energy delivery cable 482. As it is used in this description, "energy delivery cable" generally refers to any transmission medium that can be used for the propagation of signals from one point to another. In additional embodiments, energy supply 480 provides a specific energy signal for the energy delivery device 472 and energy delivery cable 482 is a suitable transmission medium to transmit the specific energy signal from the energy supply 480 to the energy delivery device 472.

In embodiments, the location of massed UA crystals 140, attached to a structure in the MP joint 130 (e.g., bone 110 and 120, cartilage 445a or other structure) may be imaged and provided to the clinician prior to the medical procedure. Imaging may also include the determination of the density and/or concentration of the free-floating UA crystals 150 in tissue 460 surrounding the MP joint 130.

The energy delivery device 472 is positioned (by the clinician or a robotic surgical device) relative to the massed UA crystals 140 and/or areas with a high density and/or concentration of free-floating UA crystals 150. Energy delivery device 472 delivers energy to the MP joint 130 wherein at least a portion of the delivered energy is directed to, and received by, the massed UA crystals 140 and/or the free-floating UA crystals 150.

The various embodiments disclosed herein, in particular the step of positioning the energy delivery device 472, may also be configured to work with robotic surgical systems. Such systems may include various robotic elements to assist the surgeon in the operating theatre and allow remote operation (or partial remote operation) of surgical instrumentation. Various robotic arms, gears, cams, pulleys, electric and mechanical motors, and the like may be employed for this purpose and may be designed with a robotic surgical system to assist the surgeon during the course of surgery or treatment. Such robotic systems may include, remotely steerable systems, automatically flexible surgical systems, remotely flexible surgical systems, remotely articulating surgical systems, wireless surgical systems, modular or selectively configurable remotely operated surgical systems, and combinations thereof.

The robotic surgical systems may be employed with one or more consoles that are in the same or remote locations. In embodiments, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console, which can be both economically advantageous, and a benefit to the patient or a series of patients.

The robotic arms of the surgical system may be coupled to a pair of master handles by a controller. The handles may be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, such as tissue resistance due to manipulation, cutting or otherwise treating, pressure applied to the tissue, tissue temperature, electrical tissue impedance, and the like. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

With continued reference to FIG. 4, energy is delivered by the energy delivery device 472 to debulk or otherwise break-up massed UA crystals 140 and/or free-floating UA crystals 150. The term "debulking," as used herein, may include breaking down UA crystals into constituent UA crystals and/or compounds (e.g., uric acid), separating UA crystal structures from the surrounding tissue and/or larger UA crystal structures, breaking at least a portion of a UA crystal mass into two or more constituent UA crystal masses, and combinations thereof. Debulking may be accomplished through the delivery of energy to create fissures in the crystal structure, burst the crystal structure, create faults in the crystal structure, separate a portion of the UA crystal mass from the original UA crystal mass, increase the mobility of one or more UA crystals, as well as breakdown of the crystalline structure that results in dissolution of UA crystals into uric acid.

The energy delivery device 472 may be classified by a property and/or type of the delivered energy. Delivered energy may be mechanical energy, electrical energy, electromagnetically induced energy, light energy or any combination thereof. Energy may be classified by the oscillation rate and/or the wavelength of the energy. Energy may be selected from one or more of ultrasonic energy, radio frequency energy, microwave energy, light energy and combinations thereof.

Energy may be classified by increasing energy or decreasing wavelength as radio waves, microwaves, infrared, visible light, ultraviolet, X-rays, gamma-rays, and the like. Microwave energy may generally be referred to electromagnetic waves in the frequency from about 300 megahertz (MHz) ($3 \times 10^{08}$ cycles per second) to about 300 gigahertz (GHz) ($3 \times 10^{11}$ cycles per second). Radio frequency may generally be referred to as electromagnetic waves in the frequency below about 300 MHz.

The term "length" as used herein may refer to electrical length or physical length. The term "electrical length" is an expression of the length of a transmission medium in terms of the wavelength of a signal propagating within a medium and may be expressed in terms of wavelength, radians or degrees. Electrical length may also be expressed as a multiple or sub-multiple of the wavelength of an electromagnetic wave or electrical signal propagating within a transmission medium. The wavelength may be expressed in radians or in artificial units of angular measure, such as, degrees. The electrical length of a transmission medium may also be expressed as its physical length multiplied by the ratio of: (a) the propagation time of an electrical or electromagnetic signal through the medium; and (b) the propagation time of an electromagnetic wave in free space over a distance equal to the physical length of the medium. By the addition of one or more appropriate reactive elements (e.g., capacitive or inductive), the electrical length may be adjusted relative to the physical length.

Various embodiments of the present disclosure may be implemented using electromagnetic radiation at microwave frequencies or at other frequencies. An electromagnetic energy delivery device including a microwave energy delivery device, according to various embodiments, is designed and configured to operate from about 500 MHz to about 10 GHz with a directional radiation pattern. Microwave energy delivery device may be configured as a dipole microwave antenna, a monopole microwave antenna, a helical microwave antenna, or any other suitable type of microwave antenna. A microwave energy delivery device may induce resonance in UA crystals 140, 150 by delivering energy at a harmonic of an UA crystal resonance frequency or other efficacious frequency, as discussed herein below.

Ultrasonic energy supplied by the energy delivery device 472 delivers mechanical energy to debulk and/or break-up massed UA crystals 140 and/or UA crystals 150. Ultrasonic instruments utilize ultrasonic waves to generate vibrations with an ultrasonic transducer along a longitudinal axis of the energy delivery device, vibrations transverse the longitudinal axis, rotary vibrations about the radial center of the transducer or any combination thereof. The resonant wave provided to the energy delivery device 472 generates high-speed mechanical movement at the distal end of the energy delivery device 472. The mechanical vibrations transmitted to the distal end of the energy delivery device 472 are very effective at transmitting the ultrasonic vibrations into the massed UA crystals 140 and the free-floating UA crystals 150 and simultaneously, generating heat energy to facilitate the dissipation and/or dissolving of the UA crystals masses 140 and/or UA crystals 150 in the aspiration fluid.

Generator 480 may be configured to provide ultrasonic energy to the energy delivery device 472. Generator 480 may include a power source, a control circuit, a drive circuit, a matching circuit, a transducer. Drive circuit is configured to produce a high-voltage, self-oscillating signal. The high-voltage output of the drive circuit is provided to the matching circuit, which contains signal-smoothing components that, in turn, produce a driving signal wave that is fed to the transducer. The oscillating input to the transducer drives the mechanical portion of the transducer. Transducer oscillates at a magnitude and frequency that sets up a resonance in the ultrasonic energy delivery device 472. In embodiments, the driving signal applied to the energy delivery device 472 may be a sine wave to achieve resonance and increase longevity of the resonating instrument and its components. The components may be selected to be resonant with one another and/or be frequency-sensitive with respect to each other.

The frequency of the high-voltage output may be selected to resonate the energy delivery device 472 at a frequency that generates resonance within the UA crystals 140, 150 as discussed in detail hereinbelow. The frequency may be related to the length and/or width of the UA crystals 140, 150 wherein application of the selected frequency breaks-down, debulks or otherwise destroys the crystalline structure of the UA crystals 140, 150.

Energy delivery device 472 may be configured to deliver other types of mechanical energy. Mechanical energy devices to mechanically debulk/break-up UA crystals 140, 150 may include drills, augers, hammers, sanders and/or any other suitable mechanical tool.

Medical procedures utilizing the systems, methods and devices described herein may increase the surface area of the UA crystals 140, 150 exposed to synovial fluid 332a (or other fluid capable of dissolving and/or removing UA crystals 140, 150 and/or uric acid). Increasing the exposed surface area aids the body's natural ability to dissolve or transport UA crystals 140, 150 and ultimately dispose through natural processes. Surface area of the UA crystal mass 140 may be increased by one or more of: removing material to form grooves, holes, ridges, channels, canals and/or any other suitable structures within or on the UA crystals 140, 150 that increases the surface area exposed to the synovial fluid 332a.

In embodiments, the energy delivery device 472 may deliver electrical energy. The delivery device 472 that delivers electrical energy may be classified by the oscillation rate and/or the wavelength of the energy.

The generator 480 may also be configured to provide electrical energy for the energy delivery device 472 and includes a power source, a control circuit, a drive circuit, an amplifying circuit and a feedback circuit. Drive circuit produces an oscillating signal at the desired frequency. The amplifying circuit amplifies the oscillating signal to a desired energy level, the control circuit controls the operation of the generator 480, and the feedback circuit measures one or more parameters of the output signal of the generator 480. Feedback parameters may include current, voltage, directed energy, reflected energy, phase and power factor, and combinations thereof.

In embodiments, the energy delivery device 472, may also be designed and configured to operate at frequencies at about or below 500 MHz. The energy delivery device 470 may be configured as a monopolar device wherein electrosurgical currents provided to the surgical site are returned to the generator 480 through a return pad attached to another portion of the patient's body. The energy delivery device 472 may be configured as a bipolar device wherein a pair of electrodes positioned at the surgical site are connected to opposite potentials of the generator 480. Electrical currents are conducted through UA crystals 140, 150 positioned between the electrodes. Electrical currents generate heat within the UA crystals 140, 150 resulting in the debulking (e.g., bursting) of the UA crystals 140, 150. Electrical currents may conduct through and heat fluids adjacent UA crystals 140, 150 and increase the ability of the fluid to suspend uric acid therein.

The physical structure of the UA crystals 140, 150 and the surrounding tissue may be exploited by selecting a particular frequency that targets and/or destroys the structure of the UA crystals 140, 150 while having little effect on the surrounding tissue. In embodiments, the frequency of the oscillating signal may be selected to resonate the UA crystals 140, 150. In further embodiments, the frequency may be related to the length and/or width of the UA crystals 140, 150 wherein application of the oscillating signal by the energy delivery device 472 breaks-down and/or destroys the crystalline structure of the UA crystals 140, 150.

With reference to FIG. 3, UA crystals 140, 150 may have needle-like structures having a crystal length of approximately 15 µm. The UA crystals 140, 150 have a resonant wavelength, $\lambda_{RES}$, of about twice the length of the structure. The surrounding medium is water, which has a speed of sound, c, of about 1500 meters per second (m/s). These values may be used to calculate the resonant frequency of UA crystals 140, 150 using formulas (1)-(4) below:

$$F_{RES} = \text{UA crystal resonant frequency} \quad (1)$$

$$F_{RES} = c/(\lambda_{RES}) \quad (2)$$

$$F_{RES} = (1500 \text{ m/s})/((0.000015 \text{ m}*2)) \quad (3)$$

$$F_{RES} = 50 \text{ MHz} \quad (4)$$

In embodiments, the energy delivery device 472 may be mechanically, ultrasonically, or electrically driven at about $F_{RES}$. In embodiments when the energy delivery device 472 is delivering ultrasonic energy, the energy delivery device 472 may resonate at the $F_{RES}$ thereby generating resonance within the UA crystals 140, 150, which causes the UA crystals 140, 150 to debulk and/or break apart. The energy delivery device 472 may indirectly transmit the ultrasonic energy at about $F_{RES}$ to the UA crystals though fluid positioned between the ultrasonic energy delivery device and the UA crystals 140, 150. Ultrasonic energy may also be transmitted through direct contact between the distal tip of the energy delivery device and the UA crystals 140, 150.

In embodiments, fluid positioned between the energy delivery device and the UA crystals 140, 150 may provide a transmission medium to transmit energy between the energy delivery device and the UA crystals. Fluid may also rapidly heat thereby increasing the saturation rate of the UA crystals 140, 150 into solution.

A driving and/or control circuit (not explicitly shown) within the energy supply 480 may use the $F_{RES}$ as a starting point. As energy application continues, the energy supply 480 may vary the frequency within a predetermined range about $F_{RES}$ to generate resonance within the UA crystals 140, 150 thereby debulking and/or breaking apart the UA crystals 140, 150 and allow removal from the MP joint 130. Energy supply 480 may incrementally increase and/or decrease the output driving the energy delivery device 472 at the $F_{RES}$ to resonate and break apart UA crystals 140, 150.

The energy delivery device 472 may be electrically driven at a harmonic of $F_{RES}$. In some embodiments, microwave energy delivery device 470 may be driven at the 19$^{th}$ harmonic of $F_{RES}$ (e.g., a frequency of about 950 MHz). In further embodiments, RF energy delivery device 472 may be driven at the third harmonic of $F_{RES}$ (e.g., a frequency of about 150 MHz).

With reference to FIG. 4, an aspiration fluid system 485 connects to the introducer lumen 470 and provides aspiration continued fluid and negative pressure to the articular space 447. Aspiration fluid supply 485a connects to the supply channel 470b of the introducer lumen 470 and aspiration fluid return 485b connects to the return channel 470c of the introducer lumen 470. Aspiration fluid mobilizes free-floating UA crystals 150 and negative pressure, provided through the return channel 470c, provides a removal pathway for removing the aspiration fluid and free-floating UA crystals 150 from articular space 447.

Aspiration fluid is provided to the articular space 447 in close proximity to the distal end of the energy delivery device 472. Energy from the energy delivery device 472 may also heat the aspiration fluid thereby increasing the ability of UA crystals 140, 150 to dissolve in the aspiration fluid, increase the rate at which the UA crystals 140, 150 dissolve in the aspiration fluid, and/or increasing the saturation level of UA crystals 140, 150 in the aspiration fluid.

In embodiments, pH manipulation therapy may be used to dissolve UA crystals 140, 150 at a predetermined pH. As such, the pH level of the aspiration fluid may be manipulated to a pH that increases the dissolution rate of the UA crystals 140, 150 in the aspiration fluid. In embodiments, aspiration fluid with a pH of about 5.5 can only support a fraction of uric acid (generated by dissolving the UA crystals 140, 150) compared to aspiration fluid with a pH of about 6.5. Saturation of uric acid in fluid plateaus at a pH of approximately 7.2. In embodiments, pH of the fluid may be adjusted to a level of from about 6.0 to about 7.2, in further embodiments, from about 6.5 to about 7.0.

Similarly, the aspiration fluid's ability to support and/or suspend uric acid increases with temperature. Aspiration fluid may be pre-heated and provided at an elevated temperature to the articular space 447 to increase the rate at which UA crystals 140, 150 dissolve into solution. The temperature increases may be limited in that the temperature of tissue within the articular space 447 does not rise above 45 degrees C. to prevent the risk of heat-generated tissue damage. Aspiration fluid may remain in close proximity to the distal end of the introducer lumen 470 in passing between the supply channel 470b and the return channel 470c formed in the introducer lumen 470. As such, the localized temperature at the distal end of the introducer lumen 470 may exceed 45 degrees C. without causing tissue damage. Temperature of the fluid may be adjusted from about 36 degrees C. to about 44 degrees C., in embodiments, from about 38 degrees C. to about 42 degrees C.

In other embodiments, the energy delivery device 472 may be removed from the introducer lumen and an aspiration device not explicitly shown) may be inserted therein to remove fluid and/or debulked portions of the UA crystals 140, 150. Aspiration device may be manipulated and/or guided about the MP joint 130 to collect and remove fluid and/or debulked portions of the UA crystals 140, 150.

After removing UA crystals 140, 150, the clinician may flush the articular space 447 to further mobilize and remove UA crystals 140 150. The synovial fluid within the MP joint 130 may be replaced with synovial fluid and/or replaced with a suitable surrogate fluid. Finally, the introducer lumen 470 is removed from the MP joint 130.

Figure 5:
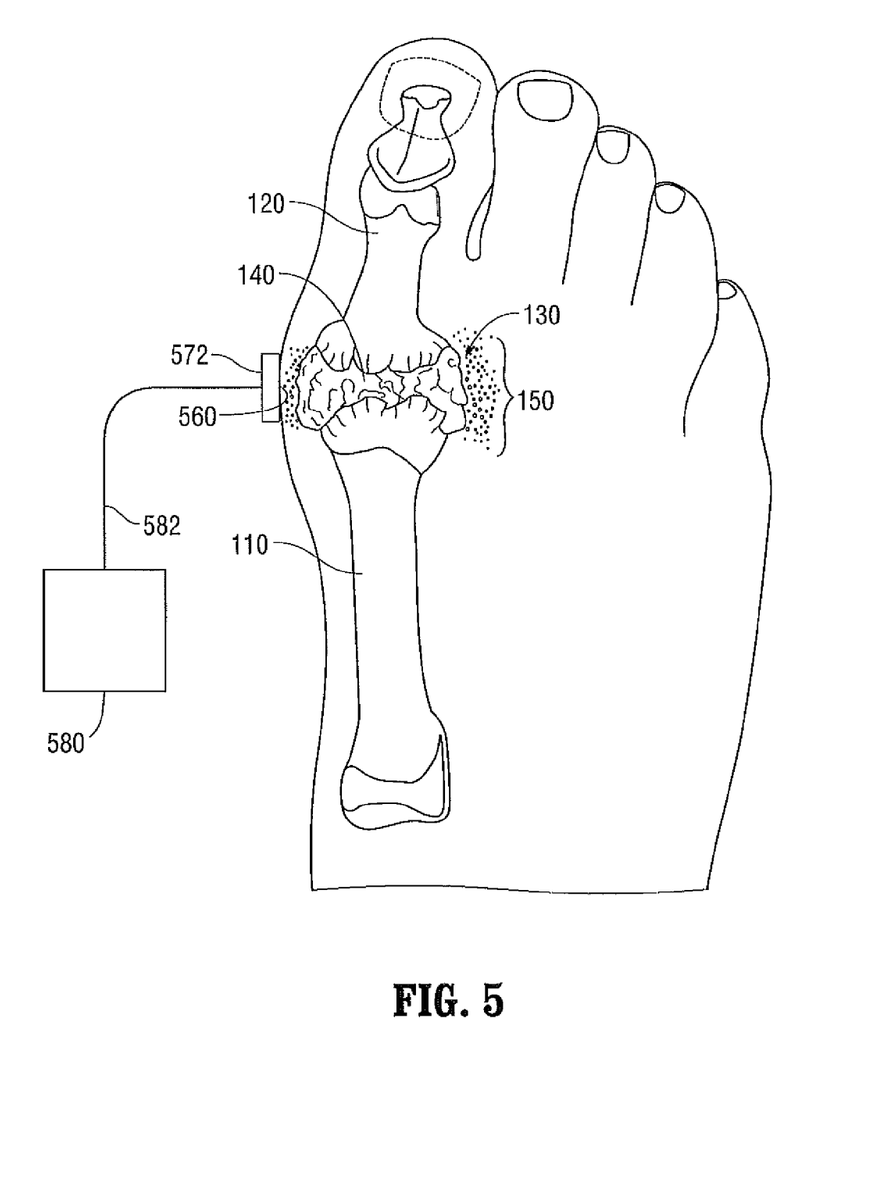
FIG. 5 illustrates a system and device for externally debulking UA crystals from the synovium of FIG. 2 according to embodiments of the present disclosure.

FIG. 5 illustrates another embodiment of treating UA crystals 140, 150 embedded in tissue. External debulking device 572 applied to the external surface 560 of MP joint 130 delivers energy to UA crystals 140 attached to the bone 110, 120 and free-floating UA crystals 150 in synovial fluid and/or embedded in soft tissue 560 surrounding the MP joint 130. The external debulking device 572 is drawn across an external surface 560 of the MP joint 130 and the energy generated by the external debulking device 572 penetrates tissue and debulks UA crystals 140, 150. External debulking device 572 may be systematically drawn in a pattern across the external surface 560 of the MP joint 130 to deliver a desirable distribution of energy to the UA crystals 140, 150.

External debulking device 572 may be utilized in conjunction with pH manipulation therapy, as discussed above, and/or utilized in conjunction with any other therapy that utilizes the body's natural ability to breakdown/remove UA crystals 140, 150 and/or uric acid.

In additional embodiments, an implemented therapy may naturally extract uric acid and external debulking device 572 may aid this implemented therapy by providing energy to release and/or debulk UA crystals 140, 150 thereby mobilizing the UA crystals 140, 150 in tissue and/or in synovial fluid of the MP joint 130.

Synovial fluid and/or surrounding tissue may also be treated to increase the fluid's ability to absorb and/or suspend uric acid. Treatment may include adjusting the pH of the synovial fluid and/or tissue, as described above. An additional step in the treatment may include increasing the amount of fluid in the synovium and/or the tissue surrounding the MP joint 130 thereby triggering the body's natural response to remove fluid including the debulked UA crystals 532 and/or uric acid produced by debulking.

A medical procedure utilizing an external debulking device 572 in accordance with embodiments described herein may include a plurality of treatments performed over a period of days and/or weeks to provide a gradual release debulking of UA crystals 140, 150 and subsequent removal of the debulked UA crystals 140, 150 and uric acid from the body.

A medical procedure utilizing the methods, system and devices described herein may be implemented early in the day to allow the body time to remove the released and/or debulked UA crystals 140, 150 and the absorbed uric acid that was dissolved into the circulatory system from the respective MP joint 130.

A medical procedure utilizing the methods, system and devices described herein may be implemented in conjunction with a dialysis procedure. A patient may receive a dialysis procedure to remove uric acid from the circulatory system before, during and/or after a method and/or procedure described herein. The patient may receive a dialysis treatment following a medical procedure utilizing the methods, systems and devices described herein to remove uric acid and suspended UA crystals released by debulking and to prevent the uric acid and/or suspended UA crystals from settling in the same or in another joint.

As various changes could be made in the above constructions without departing from the scope of the disclosure, it is intended that all matter contained in the above description shall be interpreted as illustrative and not in a limiting sense. It will be seen that several objects of the disclosure are achieved and other advantageous results attained, as defined by the scope of the following claims.

What is claimed is:

1. A method of performing a medical procedure comprising:
    positioning an energy delivery device adjacent a synovium of a bone joint having uric acid (UA) crystals, the energy delivery device configured to deliver energy adjacent the UA crystals having a resonance frequency;
    inserting the energy delivery device to the bone joint having the UA crystals through the synovium;
    applying energy to the UA crystals through the energy delivery device at a predetermined frequency thereby resonating the UA crystals;
    debulking at least a portion of the UA crystals;
    removing at least a portion of the debulked UA crystals; and
    replacing a synovial fluid of the synovium of the bone joint with a substitute fluid.

2. The method according to claim 1, wherein the energy is selected from the group consisting of mechanical energy, electrical energy, and combinations thereof.

3. The method according to claim 1, wherein the energy delivery device is a mechanical energy delivery device configured to resonate at least a portion of the UA crystals with ultrasonic energy.

4. The method according to claim 1, wherein the energy delivery device is a radiofrequency (RF) energy delivery device configured to resonate at least a portion of the UA crystals with RF energy.

5. The method according to claim 1, wherein the energy delivery device is a microwave energy delivery device configured to resonate at least a portion of the UA crystals with microwave energy.

6. The method according to claim 1, further comprising:
    providing a fluid to the bone joint, the bone joint including the UA crystals;
    suspending at least a portion of the debulked UA crystals in the fluid; and
    removing the fluid and the suspended debulked UA crystals from the bone joint.

7. The method according to claim 1, wherein debulking of at least a portion of the UA crystals further comprises separating the portion of the UA crystals from a UA crystal mass attached to surrounding tissue.

8. The method according to claim 7, wherein debulking of at least a portion of the UA crystals further comprises separating the portion of the UA crystal mass into two or more constituent portions.

9. A method of performing a medical procedure comprising:
 adjusting pH of a circulatory system fluid;
 positioning an energy delivery device adjacent a synovium of a bone joint having uric acid (UA) crystals, the energy delivery device configured to deliver energy adjacent the UA crystals having a resonance frequency;
 inserting the energy delivery device to the bone joint having the UA crystals through the synovium;
 applying energy to the UA crystals through the energy delivery device at a predetermined frequency thereby resonating the UA crystals;
 debulking at least a portion of the UA crystals;
 removing at least a portion of the debulked UA crystals; and
 replacing a synovial fluid of the synovium of the bone joint with a substitute fluid.

10. The method according to claim 9, wherein the pH is adjusted to from about 6.0 to about 7.2.

11. The method according to claim 10, wherein pH is adjusted via a process of dialysis.

12. The method according to claim 9, wherein the energy delivery device is a mechanical energy delivery device configured to resonate at least a portion of the deposit of UA crystals with ultrasonic energy.

13. The method according to claim 9, wherein the energy delivery device is a radio frequency (RF) energy delivery device configured to resonate at least a portion of the deposit of UA crystals with RF energy.

14. The method according to claim 13, wherein the RF energy delivery device is driven at a harmonic of the resonant frequency.

15. The method according to claim 9, wherein the energy delivery device is a light-based energy delivery device configured to resonate at least a portion of the UA crystals with light energy.

16. The method according to claim 9, wherein the energy delivery device is a microwave energy delivery device configures to resonate at least a portion of the UA crystals with microwave energy.

17. The method according to claim 16, wherein the microwave energy delivery device is driven at a harmonic of the resonant frequency.

18. The method according to claim 9, further comprising injecting an injection fluid into the tissue to adjust the pH of the circulatory system fluid, wherein the injection fluid has a pH different from the pH of the circulatory system fluid.

* * * * *